US00PP34562P2

(12) United States Plant Patent
Kinney

(10) Patent No.: US PP34,562 P2
(45) Date of Patent: Sep. 13, 2022

(54) ***PICEA* PLANT NAMED 'MONEVA'**

(50) Latin Name: *Picea pungens*
Varietal Denomination: MonEva

(71) Applicant: Monrovia Nursery Company Inc., Azusa, CA (US)

(72) Inventor: Ron D. Kinney, Dayton, OR (US)

(73) Assignee: Monrovia Nursery Inc., Azusa, CA (US)

( * ) Notice: Subject to any disclaimer, the term of this patent is extended or adjusted under 35 U.S.C. 154(b) by 0 days.

(21) Appl. No.: 17/577,451

(22) Filed: Jan. 18, 2022

(51) Int. Cl.
*A01H 7/00* (2006.01)

(52) U.S. Cl.
USPC ..... Plt./213

(58) Field of Classification Search
USPC ..... Plt./213
CPC ... A01H 7/00; A01H 5/00; A01H 5/12; A01H 6/00
See application file for complete search history.

*Primary Examiner* — June Hwu
(74) *Attorney, Agent, or Firm* — Cassandra Bright

(57) ABSTRACT

A new and distinct cultivar of *Picea* tree named 'MonEva' is disclosed, characterized by distinctive silver blue needles on a compact, slow growing plant. The new cultivar is a *Picea pungens*, suitable for ornamental garden purposes.

1 Drawing Sheet

Latin name of the genus and species: *Picea pungens*.
Variety denomination: 'MonEva'.

BACKGROUND OF THE INVENTION

The new cultivar is a product of chance discovery by the inventor, Ron D. Kinney. This new variety, hereinafter referred to as 'MonEva', was selected as a single unique plant in a crop of seedlings of an unpatented, unnamed *Picea pungens*. The new variety was discovered in a seedling bed at a commercial nursery in Dayton, Oreg. during April of 2008.

After identifying the new variety as a potentially interesting selection, the inventor first organized propagation of 'MonEva' by grafting at the same commercial nursery during February of 2011. The rootstock is an unnamed, unpatented *Picea abies*. The inventor continued controlled testing and propagation, assessing stability of the unique characteristics of this variety. At least four generations have been reproduced and have shown that the unique features of this cultivar are stable and reproduced true to type.

SUMMARY OF THE INVENTION

The cultivar 'MonEva' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MonEva' These characteristics in combination distinguish 'MonEva' as a new and distinct *Picea* cultivar:

1. Silver-blue needles.
2. Slow and compact grower.

COMPARISON TO PARENT VARIETY

'MonEva' is similar in most horticultural characteristics to the parent variety. Plants of the new cultivar 'MonEva' however, differ in the following:

1. Needles of the new variety are silver-blue colored, while needles of the parent variety are green.
2. The new variety is a slower and more compact grower than the parent variety.

COMMERCIAL COMPARISON

'MonEva' can be compared to the commercial variety *Picea pungens* 'Fat Albert', unpatented. The varieties are similar in most horticultural characteristics, however, plants of the new variety differ in the following:

1. The new variety is a slower and more compact grower than this comparator.

BRIEF DESCRIPTION OF THE PHOTOGRAPH

The accompanying photograph illustrates in full color a close up view of a branches of the new variety. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'MonEva' plants grown outdoors in Dayton, Oreg. Plants are approximately 1 year old, in a 1-gallon nursery container. Measurements and numerical values represent averages of typical plant types.

Botanical classification: *Picea pungens* 'MonEva'.

PROPAGATION

Time to rooting: About 90 days at approximately 20° F.
Root description: Woody, moderately well branched. Colored near RHS Brown 200C and near Grey-Brown 199B.

PLANT

Growth habit: Evergreen compact, pyramidal tree. Forms a dense, symmetrical pyramidal shaped tree.
Height: Approximately 44 cm after 1.5 years.
Plant spread: Approximately 24 cm. after 1.5 years.
Typical growth rate: Slow.
Age of plant described: About 1.5 years.
Branching characteristics: Dense branching from a single main stem. Lateral stems are held at an angle of approximately 30 to 45 degrees from the main stem.
Main stem:
*Length*.—Average 25 cm.
*Diameter*.—Approximately 1.2 cm at base, approximately 8 mm at top.
*Color*.—Near RHS Grey-Brown 199B, streaked Greyed-Orange 166C.
*Texture*.—Rough, covered in small scars from needles falling off.
*Strength*.—Very strong and flexible.
*Bark, on lower trunk of main stem*.—Moderately rough and slightly scaly. Colored near Grey-Brown 199A and N199C.
Lateral Branches:
Length of lateral branches: Average range 6 to 10 cm.
Diameter of lateral branches: Average 4 mm.
Lateral branch shape in cross section: Round.
Lateral branch strength: Flexible, strong.
Lateral branch color: Near RHS Grey-Brown 199C.
Lateral branch texture: Smooth between needles.
Internode length: Average range between 1.0 cm and 3.0 cm.
Dormant bud: Conical, About 10 to 14 mm long and 5 to 6 mm wide on 2 year old plant. Colored near Greyed-Orange 165C flushed 165B. Apex begins domed and flattens with maturity.
Terminal bud burst: Approximately March, depending upon environmental conditions.
Current year shoot growth: Approximately 4 cm to 9 cm in length. Colored near Greyed-Green 193A flushed 190A. 20 to 30 needles on average per linear cm. Emerging needles on this growth colored near Blue-Green 122C.

FOLIAGE

Leaf:
*Arrangement*.—Spirally whorled.
*Type*.—Needle.
*Shape of blade*.—Slightly triangular needle.
*Average length*.—Approximately 1.5 cm.
*Average width*.—Approximately 2 mm.
*Apex*.—Acute, sharp.
*Base*.—Obtuse.
*Attachment*.—Sessile.
*Margin*.—Entire.
*Texture of top surface*.—Glabrous.
*Texture of bottom surface*.—Glabrous.
*Leaf internode length*.—1 mm to 3 mm.
*Color*.—Young foliage: Near RHS Blue-Green 122B. Mature foliage: Near RHS Greyed-Green 191A flushed Greyed-Green 190B.
*Venation*.—Linear, indistinguishable from leaf blade.
*Durability of foliage to stresses*.—Flexible and resistant to breakage.
*Fragrance*.—Not noticeable.
*Needle curvature*.—Very weak.

FLOWER

Flowering not observed.

OTHER CHARACTERISTICS

Cone production: Not observed.
Disease and pest resistance: Neither resistance nor susceptibility observed.
Drought tolerance: No tolerance for drought.
Temperature tolerance: USDA Zones 2-8.

What is claimed is:

1. A new and distinct cultivar of *Picea* tree named 'MonEva' as herein illustrated and described.

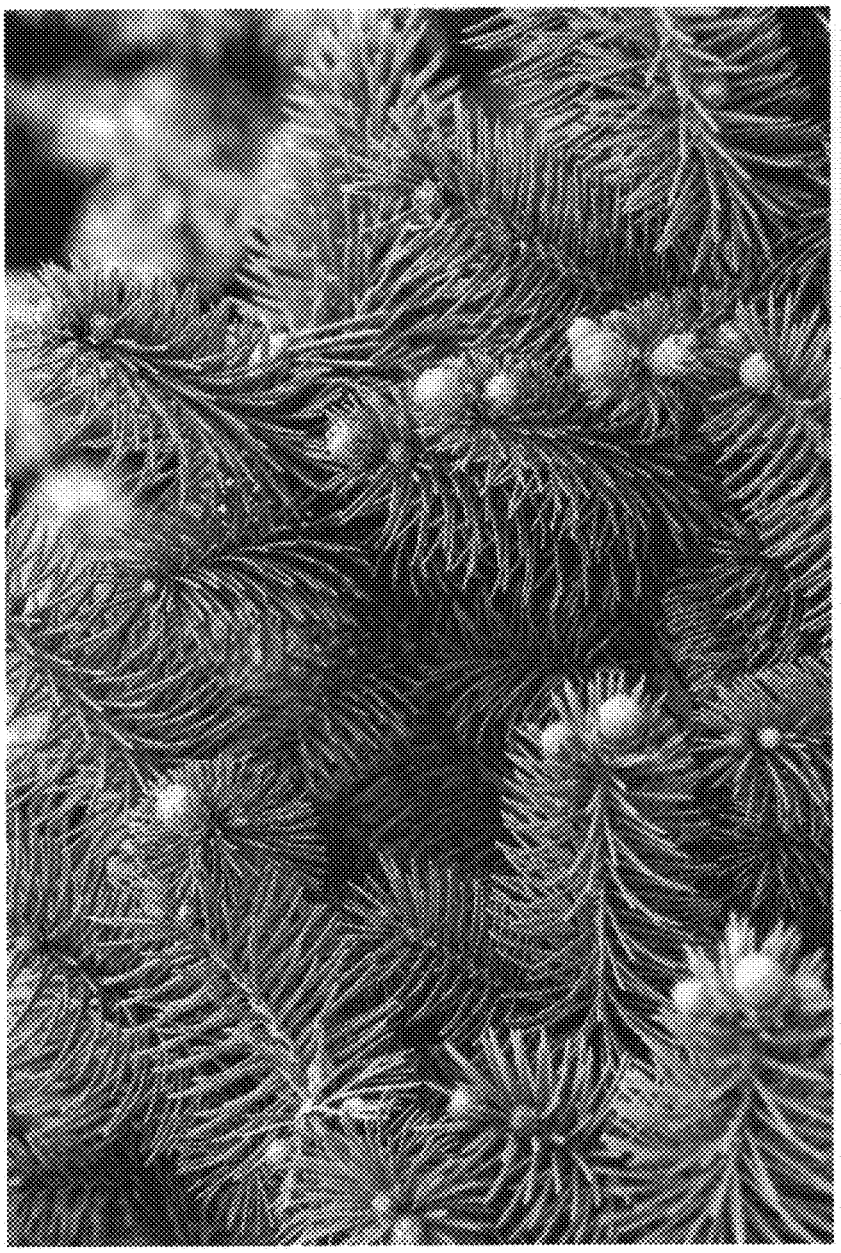

* * * * *